United States Patent [19]

Davies et al.

[11] Patent Number: 4,863,627
[45] Date of Patent: Sep. 5, 1989

[54] CLEANING AND/OR DISINFECTION OF CONTACT LENSES

[75] Inventors: David J. G. Davies; Brian J. Meakin; John E. Rees; John N. Staniforth, all of Bath, United Kingdom

[73] Assignee: University of Bath, United Kingdom

[21] Appl. No.: 946,572

[22] PCT Filed: Mar. 24, 1986

[86] PCT No.: PCT/GB86/00168
§ 371 Date: Dec. 9, 1986
§ 102(e) Date: Dec. 9, 1986

[87] PCT Pub. No.: WO86/05695
PCT Pub. Date: Oct. 9, 1986

[30] Foreign Application Priority Data

Mar. 25, 1985 [GB] United Kingdom ............... 8507678

[51] Int. Cl.$^4$ .................. A61L 2/18; G02C 13/00; A01N 59/00
[52] U.S. Cl. .................. 252/95; 252/105; 252/408.1; 252/186.3; 422/28; 422/29; 422/119
[58] Field of Search .......... 252/186.3, 186.26, 186.27, 252/188.21, 188.22, 408, 95, 105; 422/119, 28, 29

[56] References Cited

U.S. PATENT DOCUMENTS

| 3,154,494 | 10/1964 | Speak | 252/96 |
|---|---|---|---|
| 3,243,377 | 3/1966 | Stolar | 252/95 |
| 3,843,557 | 10/1974 | Fanger | 252/316 |
| 3,867,101 | 2/1975 | Herring | 23/267 A |
| 4,016,089 | 4/1977 | Regan | 252/106 |
| 4,115,293 | 9/1978 | Schoenholz | 252/102 |
| 4,295,985 | 10/1981 | Petrow | 252/105 |
| 4,568,517 | 2/1986 | Kaspar | 422/30 |
| 4,668,475 | 5/1987 | Meloy | 422/37 |
| 4,670,178 | 6/1987 | Huth | 252/95 |

FOREIGN PATENT DOCUMENTS 0124461 11/1984 European Pat. Off. .
0209071 1/1987 European Pat. Off. .
1484972 9/1977 United Kingdom .

OTHER PUBLICATIONS

*Am. J. Optom. & Physiol. Optics,* Chun et al, 64, 274–276, Apr. 1987.
*JAMA,* Stehr-Green, 258, 57–60, Jul. 3, 1987.

*Primary Examiner*—John F. Niebling
*Assistant Examiner*—I. Rodriguez

[57] ABSTRACT

A contact lens disinfecting composition in solid form for addition to water comprises a contact lens disinfecting agent which is a source of hydrogen peroxide when in water, such as sodium percarbonate; an inactivating agent in delayed-release form such as sodium thiosulphate; and a color change indicator.

12 Claims, No Drawings

CLEANING AND/OR DISINFECTION OF CONTACT LENSES

The present invention relates to the cleaning and/or disinfection of contact lenses and has particular, but not exclusive, application to the cleaning and disinfection of hydrophilic soft contact lenses, for daily and particularly extended wear. Methods and compositions provided by the invention may also be applied to hard contact lenses. It provides disinfecting compositions typically also having a cleansing action and methods of disinfecting contact lenses.

Contact lenses are thin convex lenses placed directly on the eye surface to correct sight defects. There are two general categories of contact lenses, namely hard lenses and soft lenses. Hard lenses are made of glass or, more usually, hard plastics, especially cross-linked polymethylmethacrylate. Soft lenses may be made of hydrophobic plastics, especially cross-linked dimethylpolysiloxane, but usually are made of hydrophilic plastics, especially polyhydroxyethylmethacrylate cross-linked with hydroxyethyldimethacry-late.

The disinfection of hydrophilic soft lenses using chemical agents presents a particular problem in that the lenses can absorb chemical agents from disinfecting solutions in which they are soaked. The most commonly used disinfecting solutions for soft contact lenses are aqueous solutions containing chlorhexidine (or a salt thereof) and it is well established that a sufficiently high concentration of chlorhexidine can build up in the lenses to cause irritation and, some times, damage to the eye of the lens wearer.

Extended wear lenses may contain a higher content of carboxyl groups than other soft contact lenses generally. These groups tend to bind chlorhexidine particularly strongly increasing the tendency for these lenses to build up a high concentration of chlorhexidine. To avoid the use of chlorhexidine for disinfection of such lenses, it has been proposed to use hydrogen peroxide as soaking solution for the lenses. Hydrogen peroxide is an efficient disinfectant and is particularly attractive in that its decomposition product is simply water. However, hydrogen peroxide is such a vigorous oxidising agent that it is imperative that it be thoroughly removed from the lenses before they are reinserted in the eye. Failure to do this would be likely to result in severe discomfort and possible damage to the eye.

It has been proposed to remove hydrogen peroxide from lenses which have been soaked in a solution of it by removing the lenses from the solution, placing them in a second container including a disk bearing platinum black bound thereon and adding water, or a solution of salts, buffers and preservatives. The platinum black decomposes any residual hydrogen peroxide.

The disadvantages of this process include (a) the necessity of removing the lenses from the hydrogen peroxide solution (which will be effectively sterile because of the presence of the hydrogen peroxide) to a second container which may not be sterile and may indeed contain significant contamination and (b) the danger that the neutralisation step might inadvertently be omitted by a user on some occasion leading to discomfort or eye damage. The danger of significant contamination occurring in the second container is particularly severe with extended wear lenses because of the lengthy periods of time during which the lenses are worn continuously and the disinfection apparatus is unused. The water or solutions used in the second container are also a potential source of contamination.

Other disinfection/cleansing procedures based on peroxides have been proposed. These also suffer from various disadvantages.

Thus French Patent Application 2400906 describes a composition for cleaning contact lenses containing an ene diol and a peroxide which are simultaneously added to the lens. The ene diol is intended to reduce the hydrogen peroxide over a period after disinfection has taken place. However, the presence of the ene diol at the outset of the cleansing procedure means that there is a risk of the peroxide being inactivated before cleansing and disinfection are complete. Also, as both ingredients are present intimately mixed in the formulation in dry form, there is a need to ensure that the formulation is not exposed to humidity. Should the formulation become damp, the peroxide will be inactivated. There is therefore a risk of an ineffective cleansing and disinfecting formulation being used, exposing the lens wearer to a risk of infection.

European Patent Application 0110609, describes inactivating a hydrogen peroxide solution with pyruvate after cleaning and disinfection of lenses is completed. The danger of the inactivation step being omitted still remains.

European Patent Application 0082798 describes a similar approach, suffering from the same disadvantage, but using catalase instead of pyruvate.

Where the inactivating agent is provided as a multidose solution problems arise in preserving this solution. Those materials used as preservatives for solutions tend to cause irritation for some lens wearers. Thiomersal, widely used in such solutions is such an example. Other preservative agents as sorbic acid used in such solutions are known to cause unacceptable yellow discoloration of hydrophilic lenses. In the absence of preservatives, there may be a build up of oxidation products or there may be bacterial contamination. There is therefore a need for a composition for disinfecting contact lenses which contains both a disinfecting agent and an inactivating agent which will render the disinfecting agent harmless to the eye after it has successfully disinfected lenses being treated, thus avoiding the danger of the inactivating step being overlooked and avoiding any need to transfer the lenses from the relatively sterile disinfecting agent to a separate container for the removal of the disinfecting agent or its inactivation or to have the inactivator as a conventionally presented multidose solution with the possible danger of introducing oxidative breakdown products of preservatives such as thiomersal or chlorohexidine into the eye or risking hypersensitivity reactions.

It has been proposed in European patent specification 0124461A to provide a cleansing and disinfecting composition in solid form containing an oxidising decontamination agent such as urea peroxide and a delayed release form of a reducing agent which reacts with the oxidising agent to form ophthalmically inoffensive products, both the oxidising and the reducing agent being bacteriocides and one of them also serving to destroy proteins. The lenses may be replaced in the eye after cleaning and disinfection without further treatment or rinsing.

Such compositions leave outstanding two problems. First, there remains a risk that the user may remove the lenses from the cleaning and disinfecting solution too soon so that oxidising agent is still present.

Secondly, the compositions need to be dissolved in purified water otherwise there may be gradual discoloration of or build up of deposits on the lenses due to the presence of ions such as calcium and magnesium.

Thus, failure by the user to follow exactly the instructions accompanying such compositions may lead to discomfort and to a risk of damage to the eye or to the lenses.

Accordingly, the present invention provides a contact lens disinfecting composition in solid form for addition to water comprising a contact lens disinfecting agent which is a source of hydrogen peroxide when in water, an inactivating agent capable of rendering the disinfecting agent ophthalmically acceptable, which inactivating agent is in delayed release form, and a colour change indicator such that in use a visible colour change occurs upon inactivation of the disinfecting agent by the inactivating agent.

The invention includes a method of disinfecting a contact lens comprising contacting the lens with water and a disinfecting composition of the invention as described herein.

Preferably, the colour change may be from a coloured state to a colourless state.

The indicator must be ophthalmically acceptable, at least after the action of the inactivating agent is complete, i.e. after the colour change.

The nature of the indicator will depend upon the nature of the disinfecting agent and the inactivating agent. Systems are possible employing acid/base or redox indicators as will be illustrated hereafter.

The disinfecting agent releases hydrogen peroxide when in contact with water, which may of course be present as a saline solution or a buffered salt solution.

Suitable sources of hydrogen peroxide include inorganic hydroperoxidates, ie salts with hydrogen peroxide of crystallisation. These include percarbonates, eg. sodium percarbonate ($Na_2Co_3.1\frac{1}{2}H_2O_2$), perpyrophosphates, eg. sodium perpyrophosphate ($Na_4P_2O_7.2H_2O_2$), and perborates, eg. sodium perborate ($NaBO_2.2H_2O.H_2O_2$).

They include also organic hydroperoxidates such as urea peroxide ($NH_2CONH_2.H_2O_2$), mannitol peroxide ($C_6H_{12}O_6.H_2O_2$), and peroxyacids including those of the general formula R. CO. OOH where R is alkyl, aryl or substituted aryl. Examples include perbenzoic acid and 4 methylperbenzoic acid.

More generally, examples of hydrogen peroxide yielding compounds include metal peroxides, percarbonates, persulphates, perphosphates, peroxyacids, alkylperoxides, acyl peroxides, peroxyesters and perborates.

Mixtures of two or more such compounds may be employed.

Percarbonate salts are preferred examples of compounds of this kind. In particular, sodium percarbonate is particularly preferred. The percarbonates are particularly preferable because the carbonate component can readily be neutralized by reaction with an acid.

Sodium per-pyrophosphate is another preferred compound because the pyrophosphate component can be neutralised in a similar way and because it is also a sequestering agent.

The use of sequestering agents on compositions according to the invention is described hereafter.

Preferably, therefore, in such compositions there is also present an acid to neutralise the carbonate component or phosphate component. Preferably, the acid is an organic acid and preferably the acid is present in a quantity just sufficient to neutralise the percarbonate or pyrophosphate.

For disinfecting agents which are such that the disinfecting solutions undergo a pH change upon inactivation, a pH indicator such as phenolphthalein may be used. Phenolphthalein is advantageous in that it is ophthalmically acceptable and changes from coloured in solutions of hydrogen peroxide and other basic disinfecting agents to colourless in the essentially neutral solutions produced when hydrogen peroxide is reduced by a suitable chosen deactivating agent, such as thiosulphate. The deactivating agent may include an acid to neutralise bases present.

Alternatively, a redox indicator which preferably changes from coloured in an oxidised state to colourless when reduced may be used.

They include methylene blue and triphenylmethane dyes such as brilliant green and crystal violet.

Generally, the indicators may be present in very small amounts such as to provide a 0.0001 to 0.1% concentration in the working solution, more preferably about 0.001%. An amount of 0.01 to 1 mg, e.g. about 0.1 mg may therefore be employed in a unit of compositions according to the invention.

The inactivating agent is preferably a sulphurous acid derivative, eg sulphites, bisulphites, and thiosulphate salts such as sodium thiosulphate.

More generally, the inactivating agent may be an inorganic sulphur containing reducing agent such as sodium thiosulphate, sodium bisulphite, or sodium metabisulphite, or an unsaturated compound oxidisable by peroxide such as an unsaturated carboxylic acid, eg. ascorbic acid, fumaric acid, maleic acid, pyruvic acid or sorbic acid. Ene-diols as described in French Patent Application No. 2400906 may also be employed.

Such acids can also act as a means of pH control as more fully explained hereafter.

The amount of inactivating agent present will generally not be critical but will be chosen normally to be sufficient to inactivate all the disinfecting agent provided.

The requirements of the inactivating agent are however simply an ability to react with all components of the disinfecting agent which are not ophthalmically acceptable in such a way as to produce products which are ophthalmically acceptable and to be sufficiently ophthalmically acceptable itself that any residual inactivating agent in the solution in which the contact lenses are disinfected will not be unacceptable if the quantity of inactivating agent employed is appropriate.

The presence of calcium and magnesium ions in water employed for disinfecting contact lenses can lead to the build up of opaque deposits on the lenses and accordingly disinfection is traditionally carried out with solutions prepared in purified (distilled) water rather than tap water. Apart from hardness, tap-water also often contains chlorine which can concentrate in contact lenses and causes irritation.

Accordingly, compositions according to the invention preferably contain a sequestering agent capable of sequestering calcium and magnesium ions.

The sequestering agent should be used in an amount sufficient to remove calcium and magnesium ions from the water vehicle of a disinfecting solution. Whilst the minimum amount required will vary depending upon the hardness of the water employed, an amount of at least 0.1% by weight usually will be sufficient. Suitably, the amount will be in the range of 0.1 to 1% by weight, usually 0.2 to 0.8% by weight and especially 0.3 to 0.6% by weight.

The sequestering agent can be any compound which will sequester at least calcium and/or magnesium ions from water (preferably both calcium and magnesium ions) and which is compatible with the other components and ophthalmic use of a disinfecting solution. In particular, the sequestering agent must be non-irritant to the eye at the concentrations used in lens disinfecting solutions. Preferably the sequestering agent is a complex polyphosphate, e.g. sodium hexametaphosphate, sodium pyrophosphate, or sodium tripolyphosphate. Alkyldiamine carboxylic acid derivatives may also be used for example the disodium salt of ethylenediaminetetraacetic acid.

For use with water containing or likely to contain chlorine, the compositions according to the invention preferably contain a dechlorinating agent. The dechlorinating agent may be used in an amount which prevents chlorine transference from water chlorination via the lens to the eye. The minimum amount required will vary depending upon the extent of chlorination of the water used but usually 0.001% by weight of the composition will be sufficient. Suitably, the amount will be in the range of 0.001 to 1% by weight, usually 0.005 to 0.1% by weight, especially about 0.01%.

The dechlorinating agent can be any compound which will remove chlorine from water such as tap-water and which is compatible with the other components, and ophthalmic use of the disinfecting solution. In particular, the dechlorinating agent must be non-irritant to the eye at the concentrations used in the solution. Preferably, the dechlorinating agent is a salt of sulphurous acid, eg. sodium metabisulphite, sodium sulphite, sodium bisulphite or, especially, sodium thiosulphate. The sodium thiosulphate can be in the form of its pentahydrate but preferably in its anhydrous form.

In many cases the inactivating agent will be able to act also as the dechlorinating agent.

Thus, where sodium thiosulphate or other sulphurous acid derivative is the inactivating agent, it will generally not be necessary to provide any other dechlorinating agent. If a separate dechlorinating agent is present which is incompatible with the disinfecting agent in the sense that it will destroy it or interfere with its disinfecting action, as will sodium thiosulphate, then the dechlorinating agent must be in delayed release form, as is the deactivating agent.

The composition may contain other components conventionally present in disinfecting solutions for hydrophilic soft contact lenses. In particular, it can contain an acid to adjust the pH and/or a tonicity adjusting agent. As described above, acids may be present to neutralise sodium percarbonate or other alkaline hydroperoxidates when these are the disinfecting agent. Generally, the acid will be present in an amount sufficient to provide the solution with a pH in the range of 4 to 8, preferably 5.5 to 8, especially 6 to 7.5.

Suitable acids include pyruvic, ascorbic, sorbic, tartaric, fumaric, citric, maleic, adipic and, preferably, malic acid. If required, the solution can be buffered to the required pH. As indicated above, the acid may also act to inactivate the disinfecting agent.

Usually, the composition will be chosen such as to produce with an intended volume of water a substantially isotonic solution. If it is necessary to add a component specifically to adjust the tonicity, sodium chloride can be used.

The inactivating agent is provided in delayed release form so that after the composition has been added to water, and the contact lens has been added to the mixture, the disinfecting agent will have sufficient time to disinfect the contact lens before release of the inactivating agent in sufficient quantity to halt the disinfecting action occurs.

Preferably, the composition is presented in disinfection unit form such that a single solid disinfection unit of the composition provides an adequate amount of disinfecting agent and inactivating agent for disinfecting a contact lens when added to water (tap, purified, or distilled), saline or buffered salt solution. Suitable unit forms include tablets and capsules, powders, granules and pellets.

In a tablet, the neutralising agent in delayed release form may form the core of the tablet and may be surrounded by the disinfecting agent.

In a tablet, capsule, powder, granules or pellets, there may be contained the disinfecting agent and separate particles of the inactivating agent in delayed release form.

Delayed release of the inactivating agent may be obtained by coating particles of inactivating agent with a slow dissolving coating material or by including the inactivating agent in a matrix from which it may be slowly leached. Optionally, the matrix may be coated with a slow dissolving coating so that the start of the slow release is delayed. Preferably however, the delayed release form of the inactivating agent is such that substantially no release occurs during a delay period followed by rapid and substantially complete release of the inactivating agent at the end of the delay period. Such a result may be obtained by coating the inactivating agent with a slow dissolving coating.

Materials suitable as retardants, either as coatings or as matrices, include water soluble vinyl polymers such as polyvinylpyrollidone polyvinylalcohol and polyethyleneglycol, water soluble proteins, polysaccharide and cellulose derivatives, eg. methyl cellulose, hydroxypropylmethyl cellulose, sodium carboxymethylcellulose, alginic acid and its salts and derivatives, and other water soluble naturally occuring gums. Mixtures of the above materials may be used.

Generally, such retardant materials may suitably be present at a rate of 1 to 20% of the weight of inactivating substance.

In tableting a composition according to the invention, conventional tableting additives may be employed such as sugar based excipients, e.g. lactose, surfactants, eg. sodium lauryl sulphate, polyoxy-ethyleneglycol monoalkyl ethers, alkyl-aryl ethoxylates or saccharide esters, and water soluble polymers such as polyvinylpyrollidone and polyethylene glycol.

The disinfecting agent and/or the inactivating agent may be mixed with components providing an effervescent couple to aid dissolution and break up of the formulation.

The present invention will be illustrated by the following examples of compositions falling within the scope of the invention.

EXAMPLE 1

A tablet comprises:-

-continued

| | |
|---|---|
| Sodium percarbonate | 40 mg |
| Sodium thiosulphate anhydrous | 120 mg |
| Malic acid | 40 mg |
| Sodium hexametaphosphate | 40 mg |
| Methyl cellulose | 12 mg |
| Phenolphthalein | 0.1 mg |

On dissolution in 10ml of water, the tablet yields a solution containing approximately 0.13% $H_2O_2$. The solution changes from pink to colourless upon deactivation.

EXAMPLE 2

| A tablet comprises:- | |
|---|---|
| Sodium percarbonate | 62 mg |
| Maleic acid | 60 mg |
| Sodium thiosulphate | 1 mg |
| Sodium pyrophosphate | 40 mg |
| Methyl Cellulose | 5 mg |
| Phenolphthalein | 0.1 mg |

On dissolution in 10ml of water, the tablet yields a solution containing approximately 0.2% $H_2O_2$.

EXAMPLE 3

| A tablet comprises:- | |
|---|---|
| Urea Peroxide | 97 mg |
| Maleic acid | 125 mg |
| Sodium thiosulphate | 1 mg |
| Sodium tripolyphosphate | 40 mg |
| Polyvinyl alcohol | 14 mg |
| Phenolphthalein | 0.1 mg |

On dissolution in 10ml of water, the tablet yields a solution containing approximately 0.35% $H_2O_2$.

EXAMPLE 4

| A tablet comprises:- | |
|---|---|
| Sodium perpyrophosphate | 80 mg |
| Sodium metabisulphite | 225 mg |
| Malic acid | 10 mg |
| Hydroxypropylmethyl cellulose | 20 mg |
| Phenolphthalein | 0.1 mg |

On dissolution in 10ml of water, the tablet yields a solution containing approximately 0.2% $H_2O_2$.

EXAMPLE 5

| A tablet comprises:- | |
|---|---|
| Sodium percarbonate | 40 mg |
| Sodium thiosulphate anhydrous | 120 mg |
| Malic acid | 40 mg |
| Sodium hexametaphosphate | 40 mg |
| Methyl cellulose | 12 mg |
| Crystal Violet | 0.1 mg |

On dissolution in 10ml of water, the tablet yields a solution containing approximately 0.13% $H_2O_2$. The solution changes from pink to colourless upon deactivation.

EXAMPLE 6

| A tablet comprises:- | |
|---|---|
| Sodium percarbonate | 62 mg |
| Maleic acid | 60 mg |
| Sodium thiosulphate | 1 mg |
| Sodium pyrophosphate | 40 mg |
| Methyl Cellulose | 5 mg |
| Methylene Blue | 0.1 mg |

On dissolution in 10ml of water, the tablet yields a solution containing approximately 0.2% $H_2O_2$.

EXAMPLE 7

| A tablet comprises:- | |
|---|---|
| Urea Peroxide | 97 mg |
| Maleic acid | 125 mg |
| Sodium thiosulphate | 1 mg |
| Sodium tripolyphosphate | 40 mg |
| Polyvinyl alcohol | 14 mg |
| Brilliant Green | 0.1 mg |

On dissolution in 10ml of water, the tablet yields a solution containing approximately 0.35% $H_2O_2$.

In each case, the tablet comprises the disinfecting agent tableted with slow release granules of the inactivating agent.

Such tablets may be produced by conventional pharmaceutical manufacturing techniques. For instance the inactivating agent in the form of granules may be coated with a solution or suspension of a retardant in an aqueous or organic medium, e.g. by spray granulation with the inactivating agent.

The granules of retardant and inactivating agent may then be mixed with the other ingredients together with conventional tableting aids where appropriate and may be compressed using standard machinery.

Whilst the invention has been described with reference to the characteristics of the exemplified formulations, it should be appreciated that many modifications and variations thereof are within the scope of the invention.

We claim:

1. A contact lens disinfecting composition in solid form for addition to water comprising a contact lens disinfecting agent which is capable of serving as a source of hydrogen peroxide when in water, an inactivating agent capable of rendering the disinfecting agent ophthalmically acceptable, which inactivating agent is in delayed release form, and at least 0.0001 percent by weight of the working solution of an ophthalmically acceptable colour change indicator such that in use, upon inactivation of the disinfecting agent by the inactivating agent, a visible colour change from coloured to colourless occurs, the composition upon dissolution in pure water yields an ophthalmically acceptable, non-irritating final solution having a pH of from 6 to 8.

2. A composition as claimed in claim 1 wherein the colour change indicator is a redox indicator or an acid base indicator.

3. A composition as claimed in claim 2 wherein the disinfecting agent is basic and inactivation thereof is associated with a fall in pH, and wherein the indicator is an acid/base indicator responsive to said pH change.

4. A composition as claimed in claim 3 wherein said indicator is phenolphthalein.

5. A composition as claimed in claim 1 wherein the disinfecting agent is an organic hyroperoxidate, and organic peroxide or a peroxyacid.

6. A composition as claimed in claim 1 wherein the inactivating agent is a sulphrus acid derivative.

7. A composition as claimed in claim 1 containing a sequestering agents selected from the group consisting of sequestering agents for calcium ions and for magnesium ions.

8. A composition as claimed in claim 1 in the form of a tablet having a delayed release core of inactivating agent and the disinfecting agent outside the core.

9. A composition as claimed in claim 1 in tablet capsule, granules, powder, or pellet form containing particles of disinfecting agent and delayed release particles of inactivating agent.

10. A method for disinfecting a contact lens comprising contacting the lens with water containing a composition as claimed in claim 1 and allowing the disinfecting agent to disinfect the lens and the inactivating agent to be released and to render the remaining disinfecting agent ophthalmically acceptable so as to provide said visible colour change.

11. A composition as claimed in claim 1 containing a dechlorinating agent.

12. A composition as claimed in claim 1, which on dissolution in pure water yields a final solution having a pH of from 6 to 7.5.

* * * * *